United States Patent [19]

Poss

[11] 4,262,254

[45] Apr. 14, 1981

[54] BALANCED CORONA ELECTROSTATIC FIELD SENSOR

[75] Inventor: Eliasz Poss, Guilford, Conn.

[73] Assignee: United Technologies Corporation, Hartford, Conn.

[21] Appl. No.: 52,720

[22] Filed: Jun. 27, 1979

[51] Int. Cl.³ .......................................... G01N 27/42
[52] U.S. Cl. ..................................... 324/457; 324/72; 361/218
[58] Field of Search ................ 361/218, 235; 330/9; 324/457, 458, 72, 72.5, 130, 131, 110, 115

[56] References Cited

U.S. PATENT DOCUMENTS

| | | | |
|---|---|---|---|
| 2,877,308 | 3/1959 | Reiner et al. | 330/9 |
| 3,079,556 | 2/1963 | Connelly et al. | 324/131 |
| 3,343,085 | 9/1967 | Oushinsky | 324/110 |
| 3,729,675 | 4/1973 | Vosteen | 324/457 |
| 3,857,066 | 12/1974 | Cline et al. | 324/457 |
| 4,054,835 | 10/1977 | Los et al. | 324/130 |

Primary Examiner—Michael J. Tokar
Attorney, Agent, or Firm—M. P. Williams

[57] ABSTRACT

A voltage driven corona current sensing probe, utilized to sense electrostatic charge (such as on aircraft), is provided with higher positive operating voltage than negative operating voltage to compensate for the different electron emission threshold and mobility of electrons compared to positive ions. In an AC embodiment, the voltage difference is achieved by a polarity-asymmetric voltage divider on a high voltage AC source feeding a single probe. In another embodiment, separate DC power supplies drive respective probes with different voltages.

3 Claims, 5 Drawing Figures

BALANCED CORONA ELECTROSTATIC FIELD SENSOR

The Government has rights in this invention pursuant to Contract No. N00019-77-C-0255 awarded by the Department of the Navy.

BACKGROUND OF THE INVENTION

1. Field of Art

This invention relates to electrostatic charge sensors, and more particularly to use of asymmetric high voltages on corona current sensing probes.

2. Description of the Prior Art

All bodies isolated in the atmosphere, such as aircraft, are subject to electrostatic charging due primarily to induction from the earth's field and triboelectric charging due to contact with dust, rain and charged particles in the air; additionally, aircraft are subject to ionic charging from the exhaust gases of the engines. Considering the fact that the earth's electric field may vary from 100 to 1500 volts per meter near the earth's surface (although it varies considerably and may reverse its direction and/or sign locally) and that potentials as much as 360,000 volts at 50 kilometers altitude are not unusual, it is not surprising that charge voltages on helicopters have been measured of the order of 20,000 to 50,000 volts, and in at least one case as high as 200,000 volts. Discharges between masses such as helicopter and cargo, or from masses to ground, create an undesirable possibility of igniting fuels or explosive cargoes. And, there is significant danger to earth-grounded humans, either in the handling of cargo suspended from an electrically-charged aircraft or in rescue operations.

To overcome this, it is known to measure the electrostatic charge accumulated on aircraft and other bodies, to provide a visible indication thereof and/or to neutralize the charge by means of high voltage power supplies. Typical apparatus for sensing and neutralizing electrostatic charge is described in U.S. Pat. No. 3,857,066. That system provides for a zero balance bias adjustment so that the sensing circuitry associated with the probe will provide zero output for zero electrostatic field being sensed.

The problem with systems of the general type disclosed in the aforementioned patent is that the indication of magnitude of electrostatic field is erratic with changes in atmospheric conditions in which electrostatic charge is being sensed. For instance, if the device is accurate in still air, there may be a considerable error (even 50% or more) in a high wind. Variations in water content and temperature also affect the response. And, it can be shown that no point can be found where a zero output is achieved for zero electrostatic field across all of the normal atmospheric conditions in which sensing of electrostatic charge on aircraft must be carried out.

SUMMARY OF THE INVENTION

Objects of the invention include improvements in corona current probe sensing of electrostatic charge on bodies isolated in the atmosphere, such as aircraft.

This invention is predicated on my discoveries that the current flow through a corona current probe as a function of the surrounding field has a different dependence on the magnitude of applied voltage for positive fields than that for negative fields; and that variations in response characteristics (other than gain) across a range of various atmospheric conditions can be substantially eliminated through asymmetric adjustment of applied voltage to balance the corona current response in the two polarities.

According to the present invention, the bipolar high voltage applied to a corona current interface means, such as one or more probes, in nonsymmetrical, the positive component of the voltage being higher than the negative component of the voltage. The invention encompasses single and plural probes, driven by AC and DC high voltages.

The present invention provides compensation for the lower potential required for electron emission than for electron absorption, and the lower retarding potential effect for electron space charge than that for corresponding positive ionic space charge (due to greater electron mobility). The invention also compensates for the variation in these effects with differing wind velocities as a consequence of space charge removal which increases the effective field at the probe and hence increases the corona current with higher winds. The zero balancing of circuit response to corona current in the prior art, to compensate for differences between positive and negative corona current under a single operating condition are ineffective; but balancing of the corona current effect directly, in accordance with the invention, by means of the asymmetric power supply, provides truly symmetric response, in fields of either polarity, under a variety of atmospheric conditions.

The foregoing and other objects, features and advantages of the present invention will become more apparent in the light of the following detailed description of exemplary embodiments thereof, as illustrated in the accompanying drawing.

DETAILED DESCRIPTION

Figure 1:
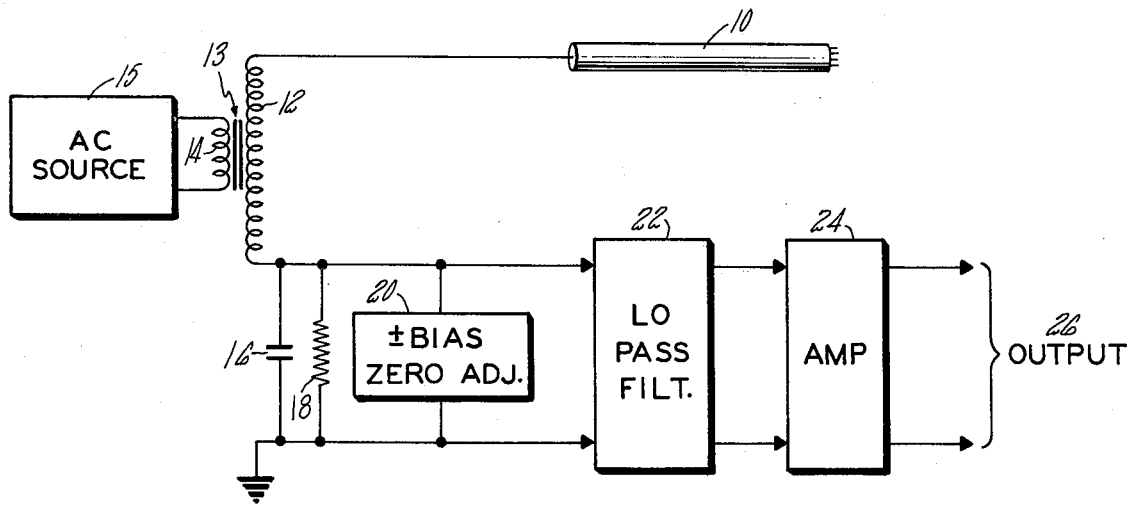
FIG. 1 is a simplified schematic block diagram of prior art corona current sensing probe apparatus, as exemplified in U.S. Pat. No. 3,857,066.

Referring now to FIG. 1, a corona current interface means, such as a probe 10, of the type typically utilized for measuring electrostatic charge on bodies isolated in the atmosphere, such as aircraft, is driven by high voltage AC provided by a high voltage secondary 12 of a transformer 13, the primary of which 14 is driven by a normal line voltage source 15 of AC power (such as 115 volts, 60 Hz or 400 Hz). If a suitably high voltage, of either polarity, is applied to the probe 10, corona current will ensue, even though there be no electrostatic field in the vicinity of the probe 10. The corona current, depending upon the characteristics of the probe, will be higher for higher applied voltage and lower for lower applied voltage, above some voltage threshold required to induce current flow. Above the threshold, in either polarity, current flow to the probe at the AC source frequency will flow through a capacitor 16, which acts as an AC bypass, and only any DC component (that is, a continuing excess of current in one polarity over that in the other) will be developed across a sensing resistor 18. As is described more fully hereinafter, such a condition (a net DC current) can exist even for zero electrostatic field, since there is a higher tendency for negative voltage to induce electron emission that there is for positive voltage to induce electron absorption. In the prior art, it has therefore been common to provide a zero adjusting bias voltage from an adjustable source 20, to compensate for the net current with a zero field, before application to a low pass filter 22 and thence an amplifier 24 to provide a useful output at terminals 26. Of course, depending upon the particular probe and circuitry being utilized, it is possible that there might be a net corona current in response to the positive portion of the applied AC high voltage, in which case the zero adjusting could still be effected for a zero output at terminals 26 when the probe 10 is known to be in a field having no electrostatic charge.

Figure 3:
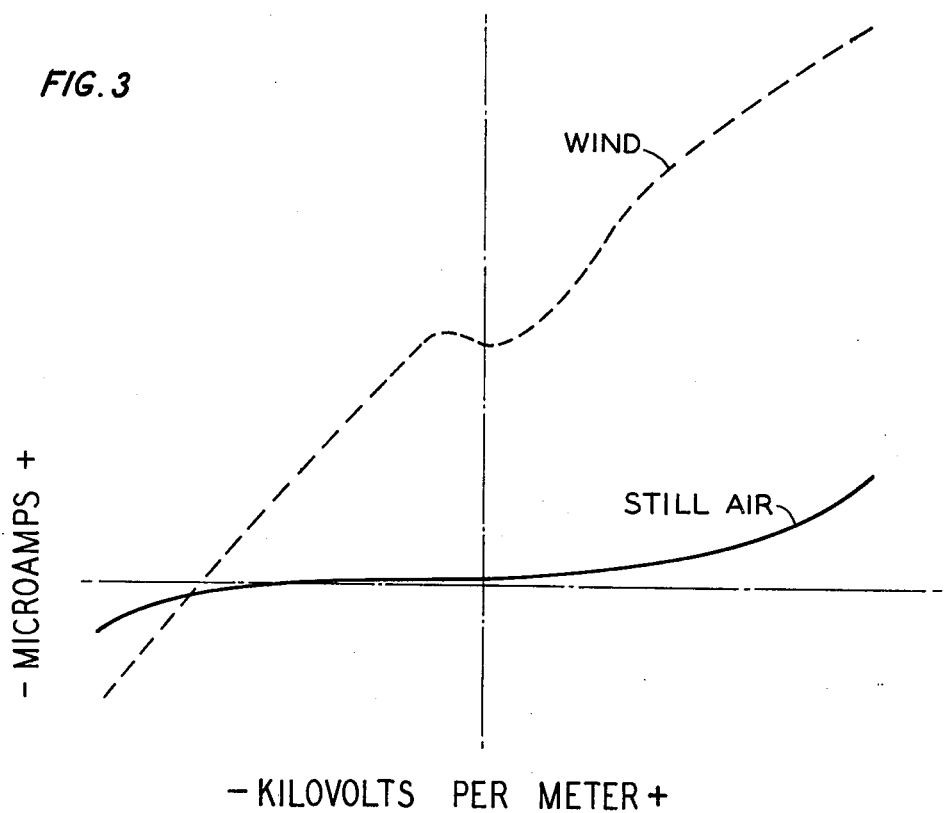
FIG. 3 is a corona current vs. electric field diagram appertaining to operation of the prior art device illustrated in FIG. 1.

The problem with circuitry of this type, which I have discovered, is illustrated in FIG. 3, wherein the ordinate is the microamperes which may flow to or from the probe 10 as a consequence of the electrostatic field around the probe set forth on the abscissa. It can be seen that if the zero adjustment is made (by the bias source 20) for zero microamperes (or zero output volts at terminals 26) in still air, this will be ineffective in a high wind (on the order of 1500 ft. per second) which provides a very significant positive output when in a zero field. To avoid confusion, the apparent favoritism of positive current (corresponding to electron emission from the probe) illustrated in FIG. 3 is a consequence of the fact that electron emission during the negative portion of the applied voltage occurs more readily than the corresponding electron absorption during the positive portion of the applied voltage. The wind clears away the emitted, opposing charges, making the effective field at the probe stronger than in still air. Note particularly that the abscissa is the magnitude of the electrostatic field, and that the applied voltage polarity does not appear on the figure.

Figure 4:
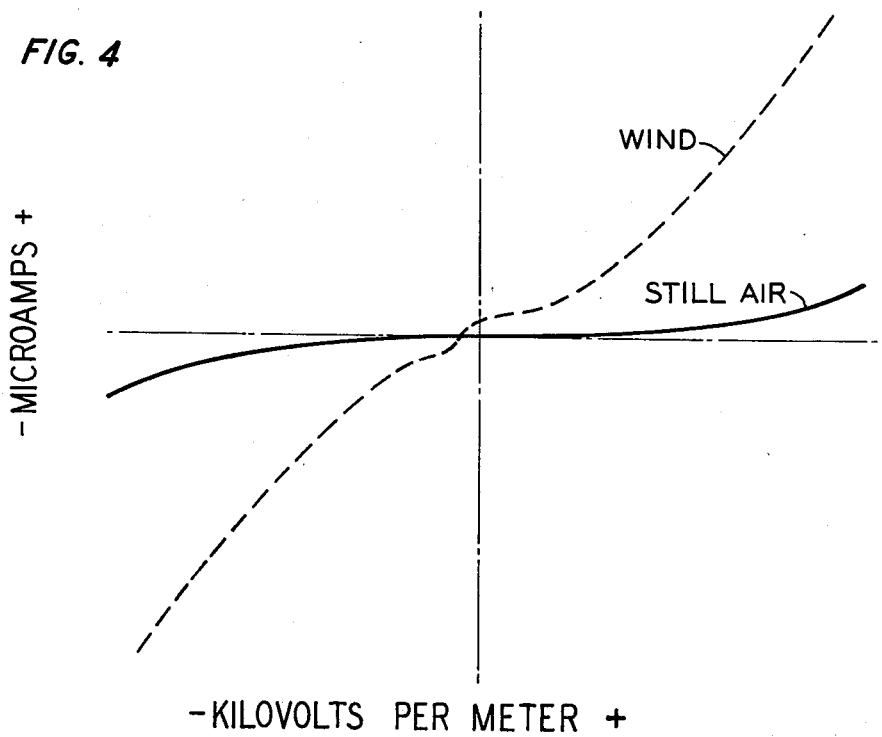
FIG. 4 is a corona current vs. electric field diagram appertaining to the present invention.

Referring to FIG. 4, the present invention provides an essentially symmetrical response of probe current as a function of field both in still air and in wind conditions, even though the response in high wind has a much higher gain or sensitivity than that in still air due to removal of the space charge near the probe by the wind.

Figure 2:
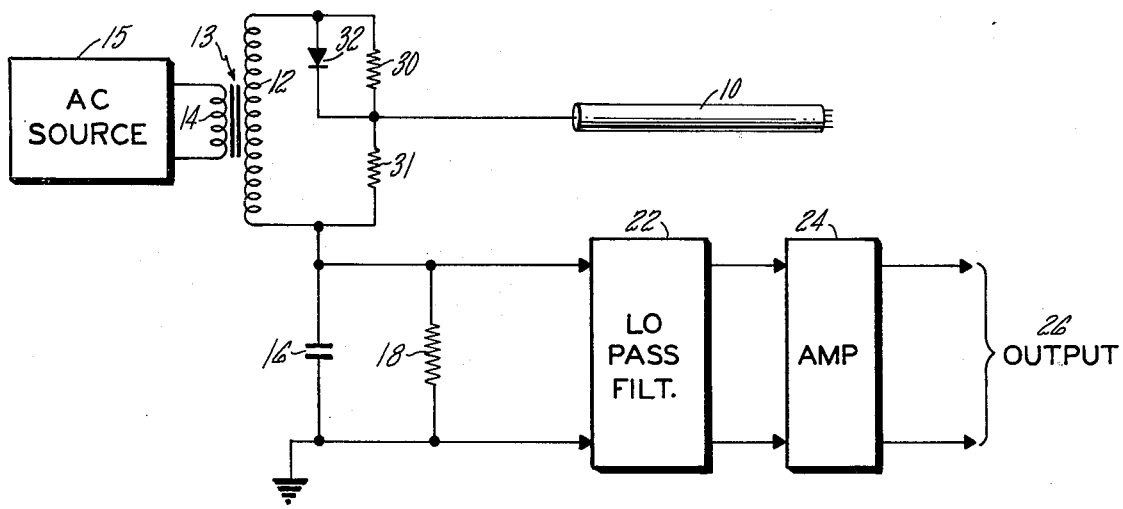
FIG. 2 is a simplified schematic block diagram illustrating the principles of the present invention.

As illustrated in FIG. 2, application of an asymmetrical AC high voltage to the probe 10 is achieved by means of a voltage divider consisting of a relatively lower resistance 30 and a relatively higher resistance 31, the lower resistance 30 being bridged by a unilateral impedance, such as a diode 32, which is poled to conduct so as to bypass the resistor 30 during the positive voltage swings, but not to affect the current flow through the resistor 30 during negative voltage swings. In one example, wherein the probe 10 consisted of a wick type of probe, such as a model RID-1 manufactured by the TCO Manufacturing Corporation, Fort Myers, Fla., balanced operation of the type illustrated in FIG. 4 herein was achieved utilizing an AC high voltage source in which approximately 4,000 volts RMS were developed across the secondary 12, in which the resistance 30 was four megohms and the resistance 31 was forty megohms, to provide peak voltages of +5656 volts and −5142 volts. Generally speaking, the higher the propensity of the probe 10 to conduct positive and negative corona currents equally, the lower the difference in the plus and minus voltages that must be provided, and therefore the smaller the resistive value of the resistor 30 may be as a fraction of the total resistance across the secondary 12.

The invention may be utilized with a wide variety of configurations, including different types of probes operated at different voltages so as to be sensitive in different environments. The particular asymmetry required (the difference in the positive and negative voltage swings of the AC high voltage supply as applied to the probe 10) may be ascertained empirically, for any given type of system (especially, a given type of probe), by placing the probe 10 between two plates encompassing a zero electrostatic field, and adjusting the relative values of the resistors 30, 31 for zero output, both in still air and in a high wind. Note that adjustment for zero balance in a high wind is virtually essential because of the extremely low sensitivity gradient (FIG. 4) for still air in contrast with the relatively high sensitivity gradient in the wind. Normally, any system of the same type will operate properly with the same driving voltages as other systems of that type.

Figure 5:
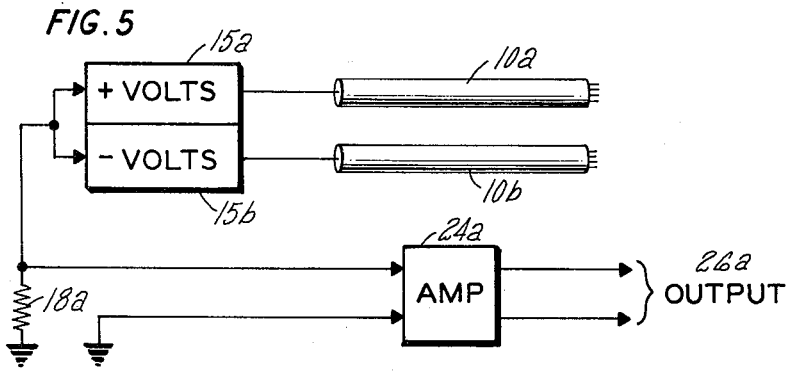
FIG. 5 is a simplified block diagram of a dual probe/supply embodiment of the invention.

As illustrated in FIG. 5, the invention may also be practiced utilizing completely separate DC power supplies 15a, 15b feeding a corona current interface means consisting of separate probes 10a, 10b, the current through either of the probes being sensed in a sensing resistor 18a in series with the power supplies and the probes. An amplifier 24a, responsive to the current through the resistor 18a, will provide an output at terminals 26a which is indicative of the current flow through either of the probes, being negative, zero or positive. Asymmetrical voltages can be selected by relative adjustment of the respective power supplies so that the combined corona current is zero in a zero field in wind and still air, as described hereinbefore.

The manner of use of the output at the terminals 26 may include a visual indicator, such as a current meter, an alarm operated above basic established thresholds of field sensed, and/or discharge apparatus of the type described in the aforementioned patent. These and other uses are immaterial to the present invention.

Also, other variations in power supplies, probes and the like may be made while practicing the invention, which is the utilization of a higher positive potential than negative potential for driving corona current interface means, without regard to whether one or more probes are used and whether the probe means are driven by AC, DC, single or multiple suppliers. Similarly, although the invention has been shown and described with respect to exemplary embodiments thereof, it should be understood by those skilled in the art that the foregoing and various other changes, omissions and additions may be made therein and thereto, without departing from the spirit and the scope of the invention.

Having thus described typical embodiments of my invention, that which I claim as new and desire to secure by Letters Patent is:

1. Improved electrostatic field sensing means having corona current interface means, power supply means for supplying bipolar high voltage to said corona current interface means of sufficient magnitude to induce current flow therein with or without any electrostatic field, and means for sensing the current flow through said corona current interface means to provide a signal indicative of the electrostatic charge in the vicinity of the corona current interface means, in which the improvement comprises:

said power supply means providing a higher positive voltage component to said corona current interface means than negative component, thereby to compensate for the difference between electron emission and electron absorption in said current interface means.

2. The invention according to claim 1 wherein said corona current interface means comprises a single corona current probe, and said power supply means comprises an AC high voltage supply connected to a nonsymmetrical voltage divider that provides higher positive voltage components to said probe than negative voltage components.

3. The invention according to claim 2 wherein said nonsymmetrical voltage divider comprises a pair of resistors and a unilaterally conductive impedance shunting one of said resistors in a direction so as to provide full positive voltage components from said AC supply to said corona current probe but only a substantial fraction of the negative voltage components from said AC supply to said corona current probe.

* * * * *